(12) United States Patent
Frei et al.

(10) Patent No.: US 12,070,255 B2
(45) Date of Patent: *Aug. 27, 2024

(54) DEVICES AND METHODS FOR MINIMALLY INVASIVE IMMEDIATE IMPLANT STABILIZATION

(71) Applicant: NEXILIS AG bei BDO AG, Grenchen (CH)

(72) Inventors: Christian Frei, Aesch (CH); Simon Zimmermann, Basel (CH); Falko Schlottig, Füllinsdorf (CH); Martin Horst, Horw (CH)

(73) Assignee: NEXILIS AG, Liestal (CH)

(*) Notice: Subject to any disclaimer, the term of this patent is extended or adjusted under 35 U.S.C. 154(b) by 472 days.

This patent is subject to a terminal disclaimer.

(21) Appl. No.: 17/371,598

(22) Filed: Jul. 9, 2021

(65) Prior Publication Data
US 2022/0061900 A1 Mar. 3, 2022

Related U.S. Application Data

(63) Continuation of application No. 15/771,732, filed as application No. PCT/EP2016/079883 on Dec. 6, 2016, now Pat. No. 11,096,733.

(30) Foreign Application Priority Data

Dec. 15, 2015 (EP) ..................................... 15199997

(51) Int. Cl.
*A61B 17/88* (2006.01)
*A61B 17/68* (2006.01)
(Continued)

(52) U.S. Cl.
CPC ........ *A61B 17/8836* (2013.01); *A61B 17/686* (2013.01); *A61B 17/8802* (2013.01);
(Continued)

(58) Field of Classification Search
CPC ............ A61B 17/8836; A61B 17/7032; A61B 17/864
See application file for complete search history.

(56) References Cited

U.S. PATENT DOCUMENTS 3,919,775 A 11/1975 Malmin
5,772,662 A 6/1998 Chapman et al.
(Continued)

FOREIGN PATENT DOCUMENTS

| EP | 1 363 543 B1 | 9/2006 |
| WO | 2009/141252 A1 | 11/2009 |

OTHER PUBLICATIONS

Written Opinion of the International Searching Authority of PCT/EP2016/079883 dated Mar. 20, 2017.
(Continued)

*Primary Examiner* — Andrew Yang
(74) *Attorney, Agent, or Firm* — Sughrue Mion, PLLC

(57) ABSTRACT

A system for the amelioration of a recess (56) is disclosed, particularly of a recess in a porous, perforate material having cavities freed by the recess, said system comprising an element (2) for generating or coupling in mechanical energy, and a cylindrical collar (4, 40) having a central recess (44,45) for receiving a guide pin (8), wherein the guide pin (8), having a cannulation (35), is provided to be inserted substantially as far as the bottom of the recess (56) under positioning using a wire (52) before mechanical energy is applied, wherein the guide pin (8), in the area of the end thereof directed toward the bottom of the recess (56), is surrounded by an amelioration sleeve (7), wherein the external cylindrical jacket surface of the amelioration sleeve (7) has substantially the same external diameter as the collar (4, 40), and wherein the guide pin (8) is received movably in the central recess (44,45) such that, when mechanical energy is applied, the collar (4,40) can be moved relative to (Continued)

the guide pin (8) in the direction toward the bottom of the recess (8) while liquefying and laterally and/or longitudinally displacing the material of the amelioration sleeve (7).

30 Claims, 8 Drawing Sheets

(51) Int. Cl.
*A61C 8/00* (2006.01)
*A61F 2/46* (2006.01)
*A61F 2/28* (2006.01)
*A61F 2/30* (2006.01)

(52) U.S. Cl.
CPC ........ *A61B 17/8872* (2013.01); *A61C 8/0009* (2013.01); *A61C 8/0089* (2013.01); *A61F 2/4601* (2013.01); *A61F 2/4675* (2013.01); *A61F 2002/2839* (2013.01); *A61F 2002/30235* (2013.01); *A61F 2/4603* (2013.01); *A61F 2002/4677* (2013.01)

(56) References Cited

U.S. PATENT DOCUMENTS

| | | |
|---|---|---|
| 2008/0039845 A1 | 2/2008 | Bonutti et al. |
| 2010/0256688 A1 | 10/2010 | Giersch |
| 2011/0077696 A1 | 3/2011 | Schlottig et al. |

OTHER PUBLICATIONS

International Search Report of PCT/EP2016/079883 dated Mar. 20, 2017.

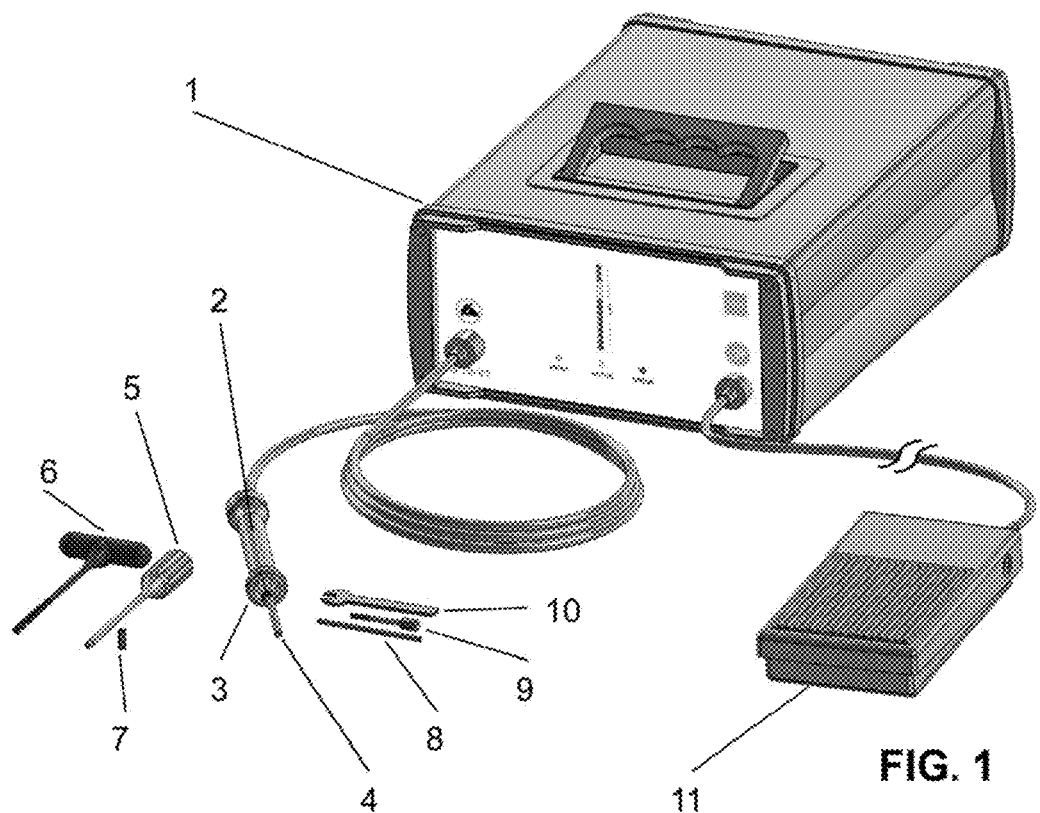
FIG. 1
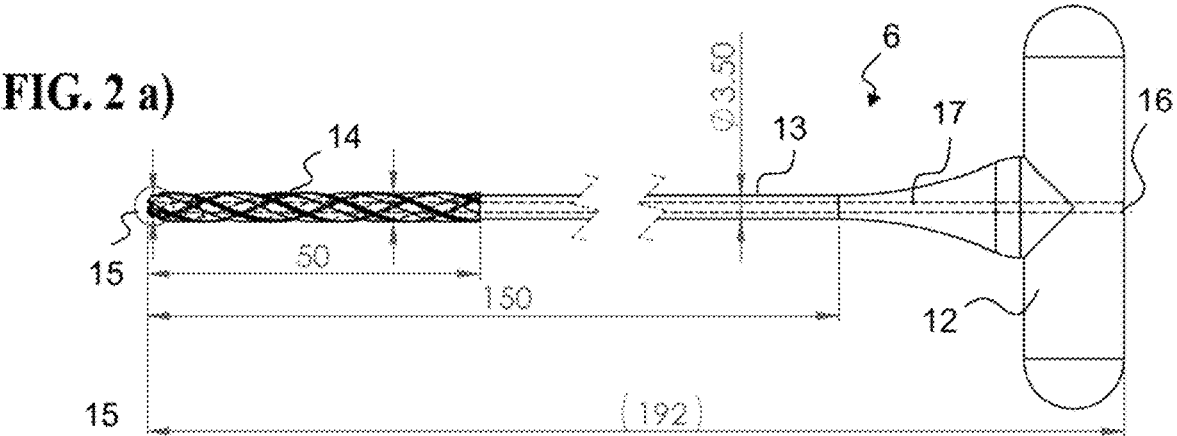
FIG. 2 a)
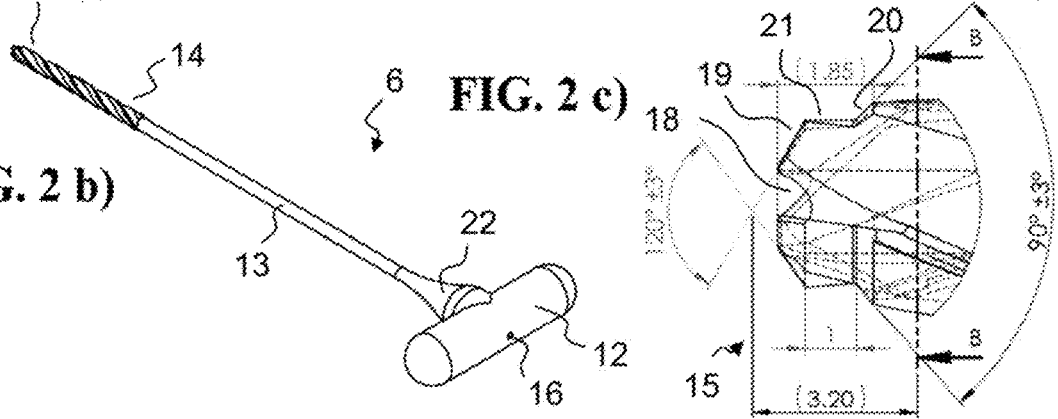
FIG. 2 b)
FIG. 2 c)

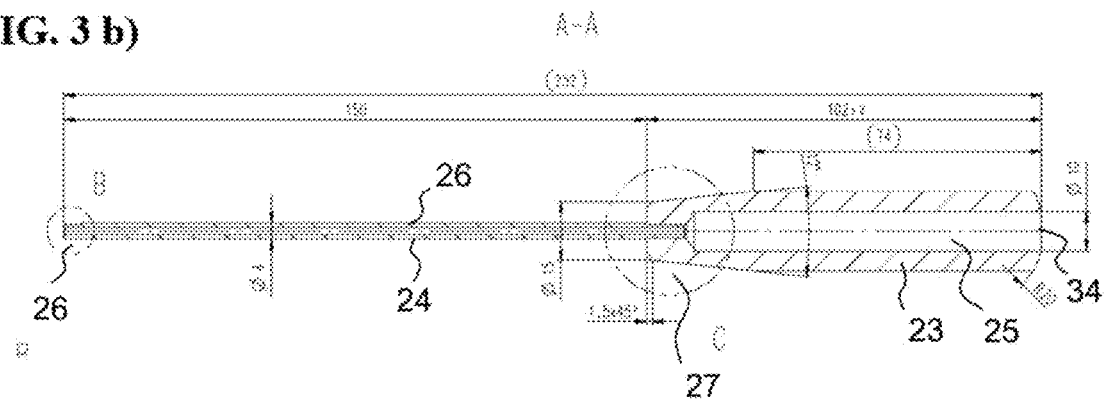
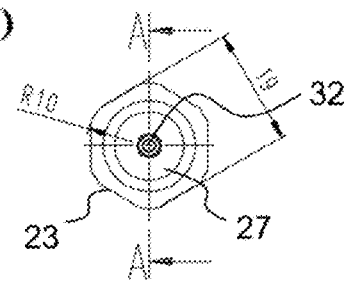
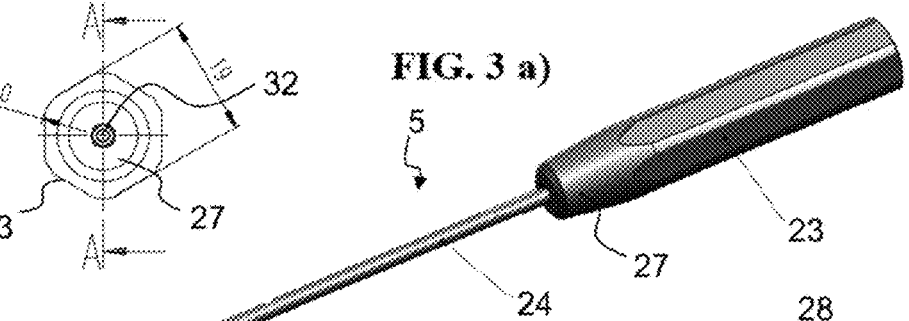
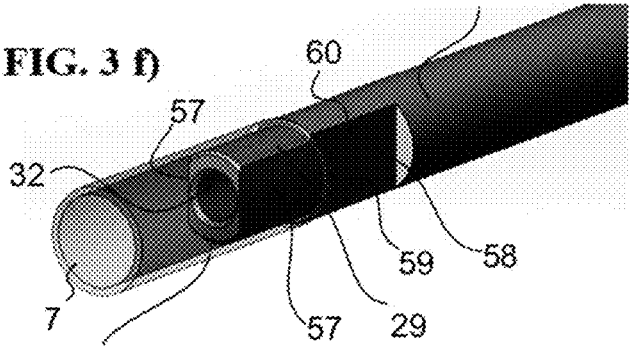
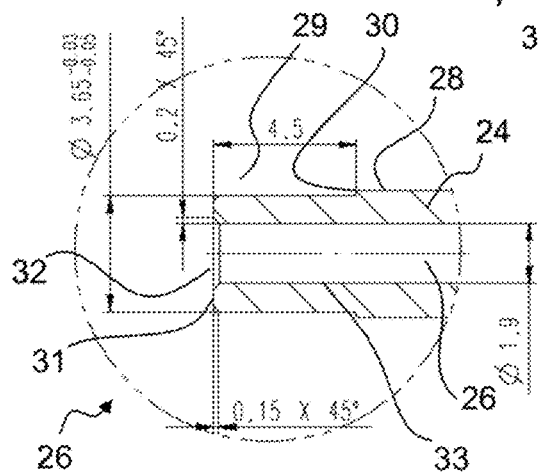
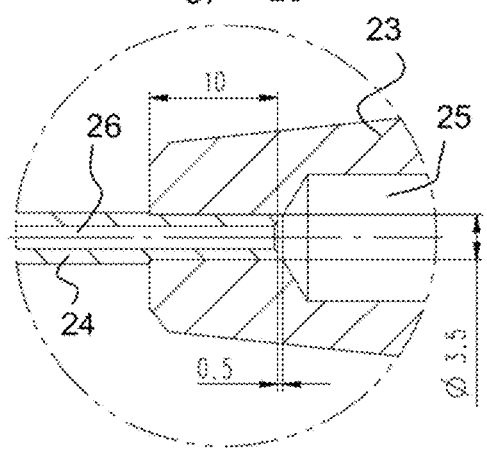

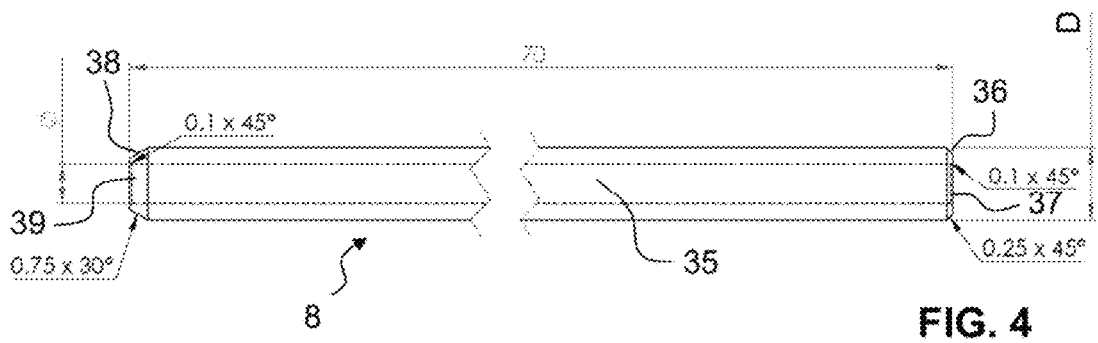
FIG. 4
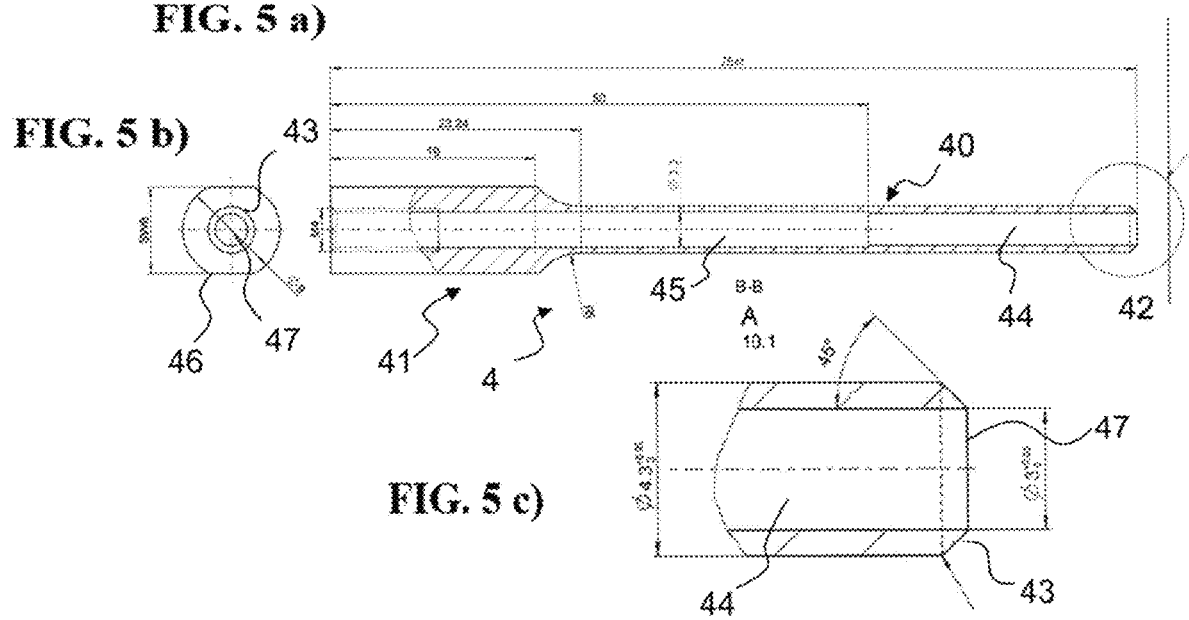
FIG. 5 a)
FIG. 5 b)
FIG. 5 c)
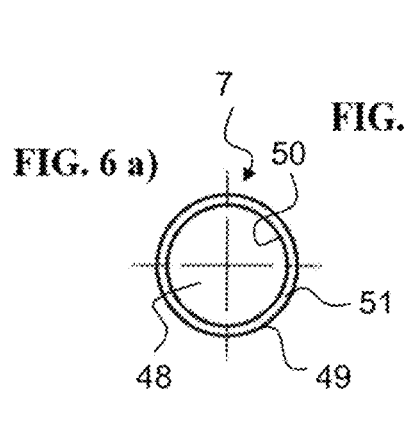
FIG. 6 a)
FIG. 6 b)

DEVICES AND METHODS FOR MINIMALLY INVASIVE IMMEDIATE IMPLANT STABILIZATION

CROSS REFERENCE TO RELATED APPLICATIONS

This is a Continuation of application Ser. No. 15/771,732 filed Apr. 27, 2018, claiming priority based on International Application No. PCT/EP2016/079883 filed Dec. 6, 2016, claiming priority based on European Patent Application No. 15 199 997.6 filed Dec. 15, 2015, the contents of all of which are incorporated herein by reference in their entirety.

TECHNICAL FIELD

The present invention relates to devices and methods for minimally invasive immediate implant stabilization in a recess, in particular in a recess of porous bone structure.

PRIOR ART

A large market that is still under-developed by medical device companies is the fixation of implant systems in poor bone quality. Demographic changes in western countries are significantly increasing osteoporosis and diabetes and therefore the incidence of poor bone quality. Osteoporosis affects an estimated millions of people in Europe, US and Japan.

Osteoporosis complicate the treatment of bone fractures dramatically, because implants developed for good bone quality fail in osteoporotic bone. The increasing number of diabetic patients further challenges the surgeons because this systemic deficit affects correct bone metabolism. Bone fracture caused by rare diseases like osteogenesis imperfecta are also very difficult to treat.

Particularly from the field concerned with securing implants in recesses in the human or animal body, for example in drilled holes in bones, it is known to screw implants, which for example are provided with a self-tapping thread, into such recesses under application of force and then to wait for the implant to become incorporated in the bone by natural healing in.

It is likewise known, particularly in the case of recesses provided in especially porous bone sections, that the primary stability may be insufficient, that is to say the stability of the implant in the recess immediately after being screwed in, that is to say before the actual incorporation process has ended.

In order to solve such problems, it has already been proposed (see, for example, EP 1 363 543) to produce the implant at least partially or even completely from a material that can be liquefied by mechanical energy. The liquefiable material can be liquefied by mechanical oscillations after the implant has been inserted into the tissue area, and in this way a form-fit connection is produced between bone and implant by virtue of the liquefied and thereafter resolidified material. A disadvantage of such solutions is the fact that very specific implants are needed to be able to carry out such methods. A further disadvantage is that the liquefiable material cannot be introduced in a sufficiently targeted manner into the desired areas and often disappears, for example, in large recesses arranged at the bottom of the recesses, without in the end contributing to the actual primary stabilization. The concept of filling recesses in a human body with the aid of a liquefiable material has in principle been known for some time, particularly in the dental field. Thus, U.S. Pat. No. 3,919,775 describes a method for filling and preparing openings with the aid of a liquefiable material which is initially pressed into the opening and which is then liquefied with the aid of a sonotrode, that is to say a device with which mechanical energy in the form of ultrasound can be introduced. The liquefied material then flows into cavities adjoining the recess and closes these cavities. In other fields where technical materials such as wood, plastics, foams, etc. are processed, such techniques are also known in the widest sense.

Furthermore WO 2009/141252 discloses a method and a device for ameliorating a recess. e.g. for preparing the recess for an implant to be fastened in that recess, in particular dental implant.

Generally in the field of implants US 2008/039845 provides a method for stabilizing a fractured bone. The method includes positioning an elongate rod in the medullary canal of the fractured bone and forming a passageway through the cortex of the bone. The passageway extends from the exterior surface of the bone to the medullary canal of the bone. The method also includes creating a bonding region on the elongate rod. The bonding region is generally aligned with the passageway of the cortex. Furthermore, the method includes positioning a fastener in the passageway of the cortex and on the bonding region of the elongate rod and thermally bonding the fastener to the bonding region of the elongate rod while the fastener is positioned in the passageway of the cortex. Inter alia the document discloses the use of a guide wire for introducing the structure to be implanted in a hole of the bone or of the tissue. There is however no disclosure of using a guide wire in the context of positioning a secondary tool of an implantation process which secondary tool is removed after the actual implantation process.

SUMMARY OF THE INVENTION

It is an object of the present invention to provide improved methods and improved devices for preparation of either predrilled or non-predrilled recesses in particular in living bone but also in other structures, in particular in porous perforate material having cavities freed by the recess.

According to one $1^{st}$ aspect of the present invention, the invention proposes a system for the amelioration of a recess, particularly of a recess in a porous, perforate material having cavities freed by the recess.

The proposed system comprises the following elements:
an element for generating or coupling in mechanical energy, and a cylindrical collar with a cylindrical jacket surface having an external diameter and having a central recess for receiving a guide pin (see further below). This cylindrical collar is used for coupling in the mechanical energy for liquefying the material of the amelioration sleeve detailed further below.

Furthermore the system comprises a guide pin, having an axial central through bore in the form of a cannulation, and which is provided to be inserted substantially as far as the bottom of the recess under positioning using a wire inserted into said cannulation of the guide pin, before mechanical energy is applied.

Furthermore the system comprises an amelioration sleeve made from a material that can be liquefied by mechanical energy. The guide pin, in the area of the end thereof directed toward the bottom of the recess, is surrounded by the amelioration sleeve, and the external cylindrical jacket surface of the amelioration sleeve has substantially the same external diameter as the collar.

Furthermore the guide pin is received movably in the central recess of the collar such that, when mechanical energy is applied, the collar can be moved relative to the guide pin in the direction toward the bottom of the recess while liquefying and laterally and/or longitudinally displacing the material of the amelioration sleeve.

Normally, cylindrical collar has a circular cylindrical jacket surface, and the amelioration sleeve has a circular cylindrical jacket surface, and the external diameter of the collar and of the amelioration sleeve are substantially the same as the internal diameter of the recess to be ameliorated.

Preferably, the collar, at its distal end, has a circumferential distal edge tapering toward said distal end. This distal edge can be either straight, and therefore conical, or curved, in particular concave or convex, or may also have a radially stepped design at the distal end, wherein the circumferential distal edge of such a stepped design is arranged at the step transition.

Normally the amelioration sleeve is a simple hollow cylinder made of the liquefiable material.

The proposed Immediate Stabilization System solution is like the application of an implantable polymeric tube around the original implant. By applying ultrasonic energy, the polymeric tube (amelioration sleeve) is moulded into the pores of the host bone recess forming a strong and uniform bond with the adjacent bone. The original device is implanted in the created denser bony environment leading to enhanced immediate stability.

As a platform technology it can be used in dental, trauma, spinal and other orthopaedic applications without any change of original implants. The immediate stabilization system considered here focuses on the stabilization of pedicle screws with the purpose of vertebral fracture fixation within the course of a clinical trial, however it can also be used for other types of implants.

Similar methods as for example the augmentation with PMMA (bone cement), which represents the gold standard, exhibit major drawbacks regarding cytotoxic effect of the monomer, exothermic reaction (~70° C.), completely rigid implant-tissue interfaces as well as the application of non-degenerative materials. The immediate stabilization method proposed here uses an ultrasonic melting process of amelioration sleeves for example in the form of polylactide tubes that lead to a well-controlled melt into for example the trabecular bone structure. Due to the ultrasonic energy input, thermal impact to the bone tissue is regionally and temporary limited and the application of polylactide enables the material to be naturally degraded after the advantage was taken from the improved primary stability.

The general concept of the immediate stabilization system method and device is based on the insertion of a polymer-tube (amelioration sleeve) into an optionally preprocessed drill hole, to melt the polymer by using an ultrasonic device (sonotrode) and to insert the standard implant afterwards.

The technological process combines the liquefaction and resorbability of a polymer to achieve better primary stability compared to implants alone. The proposed method allows for minimally invasive high precision positioning and therefore optimum use of the material of the amelioration sleeve and optimum penetration of the liquefied material into the porosity of the structure surrounding the recess to be ameliorated. The ultrasonic energy causes liquefaction of the polymer in contact with the bone. The resorbable polymer material penetrates into the cancellous bone structure. Re-solidification initiates as soon as the supply of ultrasonic energy is stopped.

During the "traditional" healing time of the fractured vertebra following the implant placement, the natural osteointegration processes occurs. Furthermore the polymeric material degrades and new bone formation takes place filling the hollows and holes previously filled by the polymeric material. This means that the secondary stability, which is responsible for the long term stability of the implant, is achieved by the traditional biomechanical interlock between the implant surface and the bone.

More particularly, the proposed system preferably comprises at least one of or preferably a combination of several or all the following elements:

US generator: The US (ultrasound) generator provides the handgrip (converter) with power in the form of AC voltage with a frequency of for example in the range of 30-100 kHz, e.g. 35 kHz or 70 kHz. The activation of the US power can be controlled by a foot pedal or by a manual control located on the handgrip of the sonotrode. The US parameters are configured by means of the generator's software/firmware for an optimal application in the ISS Study System and normally cannot be changed by the user.

Foot pedal: The (optional but preferred) foot pedal works as trigger for the US generator. By pressing the foot pedal, the US generator is activated and the US power is delivered to the handgrip (converter). The foot pedal includes the cable for the connection to the US generator.

Handgrip: The handgrip preferably includes a converter to transform the electrical AC power into mechanical oscillation. The mechanical US oscillation is preferably applied to a sonotrode, which is fixed at or coupled with the piezo of the handgrip frontside. The Sonotrode can be either directly coupled with the piezo or indirectly via a metal element (e.g. cylinder, made of stainless steel or titanium) between the piezo and the sonotrode. The handgrip may include a cable for the connection to the US generator, and/or it may also be cannulated for having a K-wire passing through the corresponding bore. The handgrip may also include an actuator (in full or partial replacement/supplement to the foot pedal) trigger for the US generator.

Protection sleeve: Typically for the minimally invasive techniques envisaged for the proposed system the hole to be ameliorated is located in a bone or hard tissue which is buried and/or covered by a layer of soft-tissue. In other words above the actual bone to be handled and treated there is a layer of soft-tissue (skin, muscles, connective tissue, etc.) which also comprises a hole essentially of the same diameter, typically of a somewhat larger diameter, than the hole in the bone to be ameliorated. It can be problematic if the sonotrode contacts this surrounding soft-tissue above the bone to be treated, since contact with soft-tissue can lead to heating and burning of the soft-tissue. In order to avoid this, a protection sleeve can be provided. This protection sleeve is a hollow tube, e.g. made of metal, which has an inner diameter which is equal or preferably somewhat larger than the outer diameter of the hole in the bone to be ameliorated. This protection sleeve can be made of metal or a suitable plastic material. The protection sleeve can then be inserted into the surficial hole in the soft-tissue until contacting the bone at the edge of the hole to be ameliorated and on the surface of the bone and to abut with this surficial portion of the bone surrounding the hole therein. In order to avoid contacting with the sonotrode the inner surface of the central bore in the protection sleeve can either be provided with distance keeping elements, e.g. axial ridges made of a suitable plastic material, or the protection sleeve may also be attached to or part of the handgrip, for example mounted on the handgrip in a way such that the protection sleeve can only be moved axially relative to the sonotrode tip portion without touching the sonotrode.

Covering-ring: The handgrip further may include a covering-ring which is fixed at the front side of the handgrip casing, for ensuring a sterile handling during the treatment, the covering ring can be sterilized and can take the function of sealing the handgrip to prevent penetration of human liquids into the handgrip, in particular for the situation where the handgrip as a whole cannot be sterilized. If the handgrip as a whole can be sterilized, no such covering ring is necessary, but can still be advisable for sealing purposes.

Sonotrode: The sonotrode transmits the mechanical oscillation of the piezo (in the handgrip), with a specific amplitude to its tip and further to the ISS sleeve (amelioration sleeve) which is molten by the transmitted US energy.

An optional depth scale at the lateral surface of the sonotrode can be used to show the depth that needs to be reached during the ISS melting process, in relation to the length of the later implanted pedicle screw. A sleeve may be provided around the sonotrode in certain regions to avoid contact with bone and/or tissue where undesired. The depth scale can be provided to be considered relative to such a protective sleeve or relative to the surface portion of the body or tissue surrounding the opening to be ameliorated.

Cleaning device: The ISS cleaning device may further be provided for the purpose of cleaning the sonotrode's inner cavity from polymer that may penetrate the gap between the guiding pin and the inner cavity of the sonotrode during the US melting process.

Torque key (also called wrench): A torque key may further be part of the system to be used to tighten the sonotrode at the handgrip by means of the grub screw. It may include torque measurement means but it may also be without specific torque measurement and/or torque maximum means.

Amelioration sleeve (ISS sleeve): The ISS sleeve preferably made of a biodegradable material such as polylactide (for example commercially available Poly (L-lactide-co-D,L-lactide 70/30)) tube which is molten and molded into the adjacent trabecular bone structure by means of ultrasound energy. By migration of the molten polymer into the trabecular bone, the effective interface surface of the subsequently implanted pedicle screw is regionally increased, leading to an increasing mechanical fixation in the vertebral body.

Guide pin (or guiding pin): The guide pin ensures that the molten polymer is pressed circumferentially into the adjacent trabecular bone structure and does not enter the inner cavity of the sonotrode or accumulates apically to the implant bed. Importantly, the guide pin is provided with a central cannulation for controlling the insertion of the guide pin with a wire previously inserted into the recess.

Insertion device. The system may further comprise an insertion device which can be used for precisely placing the ISS sleeve at the bottom of the prepared implant bed. A precise placing of the ISS sleeve and furthermore be ensured by a depth scale at the insertion device. Again the depth scale can be provided to be considered relative to a protective sleeve or relative to the surface portion of the body or tissue surrounding the opening to be ameliorated.

Reamer (also called implant bed preparatory): The system may further comprise a reamer to prepare the recess for subsequent amelioration. The ISS reamer is used prior to the ISS process, after the implant bed is prepared by means of any surgically device like an awl or a surgical drill. The reamer precisely expands the existing hole to for example a diameter of Ø 4.3 mm, which is required for ensuring a successful ISS melting process. A depth scale after the chip flute of the reamer may be used to indicate the depth until which the reamer needs to be integrated into the bone, in relation to the length of the later implanted pedicle screw. This provides for accurate knowledge of the depth of the hole to be ameliorated and also allows for better positioning of the amelioration sleeve. Again the depth scale can be provided to be considered relative to a protective sleeve or relative to the surface portion of the body or tissue surrounding the opening to be ameliorated.

The reamer may include a stepped tip portion, so the very distal end of the reamer, e.g. over an axial length of 1-5 mm, or 2-4-mm, may have an outer diameter which is smaller than the outer diameter of the actual hole to be ameliorated. The distal end of the reamer may have an outer diameter which is 10-50% or preferably 10-25% smaller than the outer diameter of the hole to be ameliorated, or it may have an outer diameter which is the same as the outer diameter of the guide pin.

According to a preferred embodiment, the guide pin of the system, at at least one end thereof, preferably at both ends, has a circumferential edge which is tapering towards the respective end of the guide pin. Preferably the inclination angle of the tapering surface with respect to the main axes of the guide pin at the circumferential edge is in the range of 20-60°, more preferably in the range of 30-45°.

According to a further preferred embodiment, the guide pin is made of synthetic polymer material, preferably of a thermoplastic material, in particular PTFE (polytetrafluoroethylene polymers) or PFA (perfluoroalkoxy polymers).

According to yet another preferred embodiment, the guide pin has an outer diameter in the range of 1.5-10 mm, preferably in the range of 2-4 mm, particularly preferably in the range of 2.5-3.5 mm.

The diameter of the cannulation of the guide pin is preferably in the range of 0.5-3 mm, preferably in the range of 1-2.5 mm, particularly preferably in the range of 1.3-2.0 mm. According to another preferred embodiment, the system further comprises an insertion device for inserting the amelioration sleeve into said recess.

Such an insertion device may have an axial central through bore in the form of a insertion device cannulation, and may be provided to be inserted substantially as far as the bottom of the recess under positioning using a wire inserted into said insertion device cannulation before said guide pin is to be inserted using the same wire.

Preferably the diameter of the cannulation of the guide pin is the same as the diameter of the insertion device cannulation.

According to yet another preferred embodiment, at its proximal end the insertion device is provided with a handle and/or at its distal end the insertion device, having a cylindrical outer surface at its distal end in as far as inserted into said recess, is provided with a narrowed portion with a reduced outer diameter and a step transition towards the proximal end so as to provide a formfitting structure for temporary holding of the amelioration sleeve for insertion.

The cylindrical narrowed portion as well as at least a portion of the cylindrical outer surface of an extension portion of the insertion device adjacent to the narrowed portion can be flattened, preferably at opposing sides. Due to this flattening in both portions a window is generated in the outer surface of the insertion device with the mounted amelioration sleeve, thereby exposing the rear edge of the amelioration sleeve at least partially over its circumference. This exposed rear edge after for insertion of the insertion device into the hole catches with the outer wall of the hole when starting to withdraw the insertion device from the hole, thereby facilitating the placing of the amelioration sleeve and releasing it in the proper position.

According to yet another preferred embodiment, the proposed system further comprises a reamer for smoothing and/or widening and/or cleaning the inner surface of the recess prior to amelioration thereof. Such a reamer may have an axial central through bore in the form of a reamer cannulation, and may be provided to be inserted substantially as far as the bottom of the recess under positioning using a wire inserted into said reamer cannulation before an insertion device for the insertion of the amelioration sleeve and/or said guide pin is/are to be inserted using the same wire. Preferably the diameter of the cannulation of the guide pin is the same as the diameter of the reamer cannulation and, in case of using an insertion device the diameter of the insertion device cannulation.

Normally the central recess is a circular cylindrical recess which is arranged coaxially with respect to the cylindrical jacket surface, and the amelioration sleeve has a circular cylindrical recess for receiving the guide pin, and the guide pin has a circular cylindrical outer surface, wherein the internal diameters of said recesses are substantially the same as the external diameter of the guide pin or the external diameter of the guide pin is 0.01-0.1 mm, preferably 0.02-0.05 mm smaller than the internal diameter of the central recess of the collar. The internal diameter of the amelioration sleeve can be somewhat larger, also to adapt the volume of material which is liquefied and introduced into the bone. Based on this the internal diameter of the amelioration sleeve can be 0.1-1 mm, preferably 0.2-0.75 mm larger than the outer diameter of the guide pin.

Keeping the guide pin and the sonotrode constant as concerns the outer diameter dimensions, it is therefore possible to choose suitable amelioration sleeves as a function of the amount of material which shall be liquefied and introduced into the porous bone structure. If for example it is found that the porosity is low, and only little material needs to be introduced, a thin-walled amelioration sleeve can be used where the outer diameter thereof corresponds to the outer diameter of the collar of the sonotrode, while the inner diameter is rather significantly larger than the outer diameter of the guiding pin. The corresponding increased play between the guiding pin and the amelioration sleeve doesn't lead to significant problems. If however for the same outer diameter of the hole, due to a high porosity of the bone, more material needs to be introduced, the same insertion device and sonotrode can be used and all that needs to be done is to choose an amelioration sleeve with the same outer diameter but with a smaller inner diameter, just somewhat larger than the outer diameter of the guiding pin. By providing a set of amelioration sleeves with the same outer diameter but with increasing wall thickness up to an inner diameter which is just somewhat larger than the outer diameter of the guiding pin, a set of amelioration sleeves can be provided which can be used adapted to the porosity of the bone and which can be handled by the same sonotrode and guiding pin.

The guide pin can preferably be pushed into the collar at most as far as an abutment position, wherein the guide pin, in this abutment position, ends at most flush with the distal end of the collar, but preferably protrudes beyond this end, wherein the protruding length in the abutment position is preferably at least 1-10 mm, preferably 2-5 mm.

According to yet another preferred embodiment, the external diameter of the collar is in the range of 1-80 mm, preferably in the range of 2-10 mm.

According to another preferred embodiment the external diameter of the guide pin is 0.1-20 mm less, preferably 0.1-2 mm or 0.5-1 mm less, and the amelioration sleeve has a thickness such that the external diameter thereof is the same as the external diameter of the collar, wherein the amelioration sleeve, at least in some sections, preferably has a wall thickness in the range of 0.1-1 mm.

Preferably, the element generates mechanical energy in the form of vibration energy and/or oscillation energy with frequencies in the range of 1 kHz-10 GHz, preferably in the form of ultrasonic oscillations in the frequency range of 10 kHz-100 MHz or 20-150 kHz, particularly preferably in the range of 30-70 kHz or 35-70 kHz or 50-70 kHz, which are transmitted in the longitudinal, transverse or rotational direction, or in a combination or linear combination of these directions, preferably substantially exclusively in the longitudinal direction, to the collar and/or guide pin and thus indirectly to the amelioration sleeve, wherein the collar is preferably secured on the sonotrode, and the guide pin can be moved therein, or the guide pin is secured on the sonotrode, and the collar can be moved, or collar and guide pin are secured on a sonotrode or coupled thereto. The amelioration sleeve can be made from a material that can be liquefied by the mechanical energy, particularly by oscillation energy, and that is selected from the following group: thermoplastic biocompatible polymers such as polyolefins selected from PP, LDPE, HDPE, UHMWPE, polyoxymethylene, polyaryl ether ketones, such as PAEK, PEEK, PEKK, polycarbonates, polyacrylates, such as PMMA, polyamides, polyesters, such as PET, PBT, polysulfones and polyether sulfones, such as PSU. PES and/or biodegradable or resorbable polymers, such as poly(L-lactide) (PLLA), poly(D,L-lactide) (PDLLA) and/or stereocopolymers thereof with a variable ratio of the L and D,L part, polyglycolides (PGA) and/or copolymers, such as polyglycolide-co-trimethyelene carbonate (PGA-co-TMC), poly(D,L-lactide-co-glycolide) (PDLLA-co-PGA) and poly(L-lactide-co-glycolide) (PLLA-co-PGA), poly(e-caprolactone), polydioxanones, trimethylene carbonates (TMC), polyorthoesters (POE) and other polyanhydrides, resorbable polymers which are produced from natural raw materials, such as modified polysaccharides (cellulose, chitin, dextran, starch), or a combination or a mixture of these materials.

One or more pharmaceutical active substances can preferably also be provided in this material of the amelioration sleeve or this material mixture or applied as a layer on this material, wherein these pharmaceutical active substances are preferably released in a controlled manner.

Furthermore the present invention relates to a guide pin for use in a system as outlined above, wherein the guide pin preferably at at least one end thereof, preferably at both ends, has a circumferential edge which is tapering towards the respective end of the guide pin. Preferably the inclination angle of the tapering surface with respect to the main axes of the guide pin at the circumferential edge is in the range of 20-60°, more preferably in the range of 30-45°.

According to a preferred embodiment the guide pin is made of synthetic polymer material, preferably of a thermoplastic material, in particular PTFE and/or PFA.

According to yet another preferred embodiment, the guide pin has an outer diameter in the range of 1.5-10 mm, preferably in the range of 2-4 mm, particularly preferably in the range of 2.5-3.5 mm.

The diameter of the cannulation of the guide pin can be in the range of 0.5-3 mm, preferably in the range of 1-2.5 mm, particularly preferably in the range of 1.3-2.0 mm.

In addition to that, the present invention relates to a sterile package with a guide pin as defined above, but also to a sterile package with an amelioration sleeve as defined above, or an insertion device as defined above or a reamer as defined above.

Furthermore, the present invention relates to a method for operating a system as defined above. Preferably this method is characterized in that a wire (the so-called K-wire or Kirschner wire) is centrally inserted into a recess and pushed into the very bottom thereof. If needed the inner surface of the recess is then prepared for amelioration by using a reamer with a central cannulation which cannulation is pushed over said wire for controlled insertion of the reamer into the recess, the reamer being rotated when positioned in the recess until the desired preparation of the recess is terminated, and subsequently the reamer is taken out while keeping the wire in place. The reamer may include a stepped tip portion, so the very distal end of the reamer, e.g. over an axial length of 1-5 mm, or 2-4-mm, may have an outer diameter which is smaller than the outer diameter of the actual hole to be ameliorated. The distal end of the reamer may have an outer diameter which is 10-50% or preferably 10-25% smaller than the outer diameter of the hole to be ameliorated, or it may have an outer diameter which is the same as the outer diameter of the guide pin. The guiding pin may either also comprise such a distal end with a stepped tip portion the outer diameter thereof corresponding to the outer diameter of the step portion of the reamer. Or, in case the step portion of the reamer has a diameter which is the same as the outer diameter of the guide pin, there is no such need of having a guide pin with a stepped tip portion. The advantage of providing such a stepped hole in preparation for the amelioration processes that the guide pin can then be inserted into that somewhat more narrow portion of the hole, is then very tightly fixed in that hole, and apical migration of liquefied material into the bottom of the hole to be ameliorated can essentially be avoided. Subsequent to this, an insertion device having an amelioration sleeve mounted at the distal tip portion thereof and having a central cannulation can be used and is pushed with said cannulation over said wire for controlled insertion of the insertion device with the amelioration sleeve into the recess and positioning the amelioration sleeve in the bottom region of the recess, and subsequently taking out the insertion device while keeping the amelioration sleeve in the recess and keeping the wire in place.

As an alternative the amelioration sleeve can directly be mounted on the guide pin and can be inserted into the recess together with the guide pin.

Then the guide pin is pushed with its cannulation over said wire for controlled insertion of the guide pin and for insertion of the distal portion thereof into the positioned amelioration sleeve in the recess, for the situation where the insertion device has been used, wherein the recess has an internal diameter corresponding substantially to the external diameter of collar and amelioration sleeve, until the guide pin abuts against the bottom of the recess and/or engages in a guide taper arranged at the bottom of the recess.

Then, with simultaneous liquefying of the amelioration sleeve by applied mechanical energy, preferably by applied ultrasound, and with pushing of the distal end of the collar into the recess, liquefied material is introduced into cavities, particularly lateral cavities, adjoining the recess.

The above method can be a surgical method but it can also be a non-surgical method, e.g. applied to a recess which is a recess in an at least partially porous technical material, including wood or wood-like material, or foam material, particularly a polymer foam, a composite foam and/or a metal foam, or in an at least partially dead or living porous human or dead or living animal bone section, particularly in a jaw bone or a spinal column bone, and in that the recess is preferably generated at least partially by preliminary drilling. Further embodiments of the invention are laid down in the dependent claims.

BRIEF DESCRIPTION OF THE DRAWINGS

Preferred embodiments of the invention and are described in the following with reference to the drawings, which are for the purpose of illustrating the present preferred embodiments of the invention and not for the purpose of limiting the same. In the drawings, FIG. 1 shows the kit of parts;

FIGS. 2a)-2c) show in 2a) shows a side view of the reamer, in 2b) a perspective view and in 2c) a detailed view of the tip portion of the reamer, FIGS. 3a)-3f) show in 3a) a perspective view of the insertion device, in 3b) an axial cut thereof and in 3c) a front view, in 3d) the details of an axial cut through the tip portion and in 3e) the details of an axial cut through the transition portion of the insertion device, and in 3f) a modified tip design of the insertion device;

FIG. 4 shows a side view of the guiding pin;

FIGS. 5a)-5c show in 5a) an axial cut through the sonotrode, in 5b) a front view of the sonotrode, in 5c) the details of an axial cut through the tip portion of the sonotrode;

FIGS. 6a)-6b) show in 6a) an axial view on the stabilization sleeve and in 6b) an axial cut thereof;

DESCRIPTION OF PREFERRED EMBODIMENTS

Figure 7:
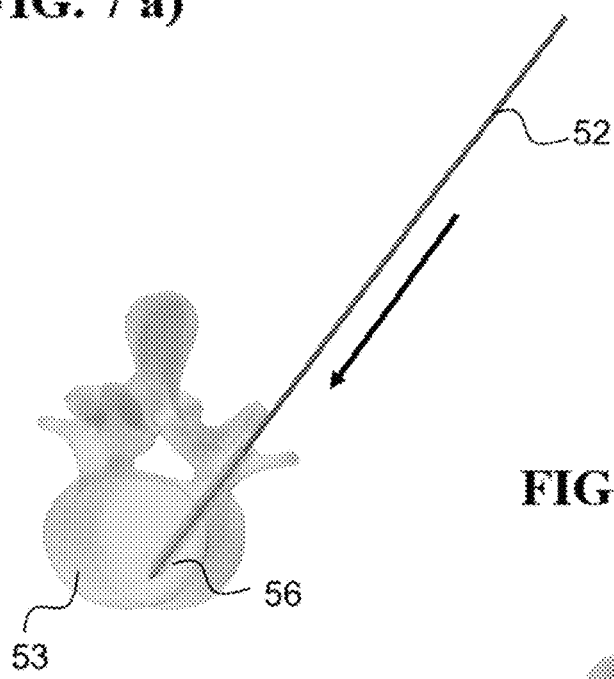
FIGS. 7a)-7l) show the individual steps when using these elements for amelioration of an opening.
Figure 7:
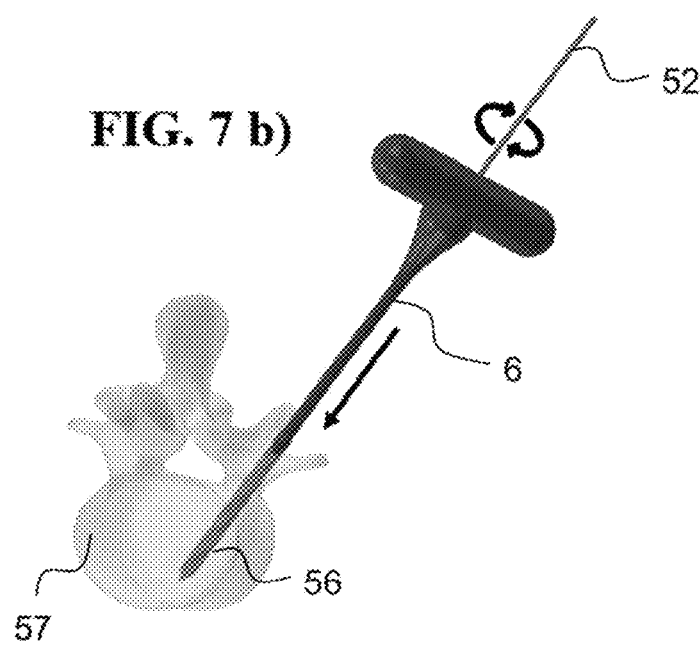
Figure 7:
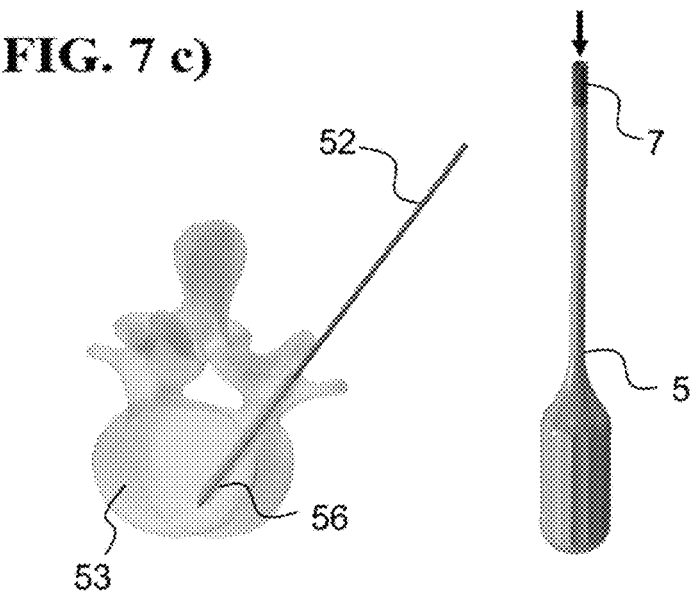
Figure 7:
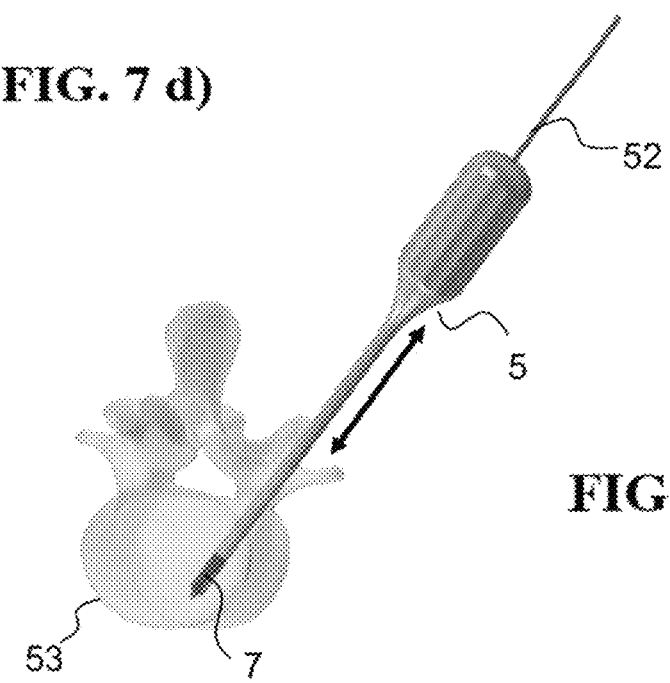
Figure 7:
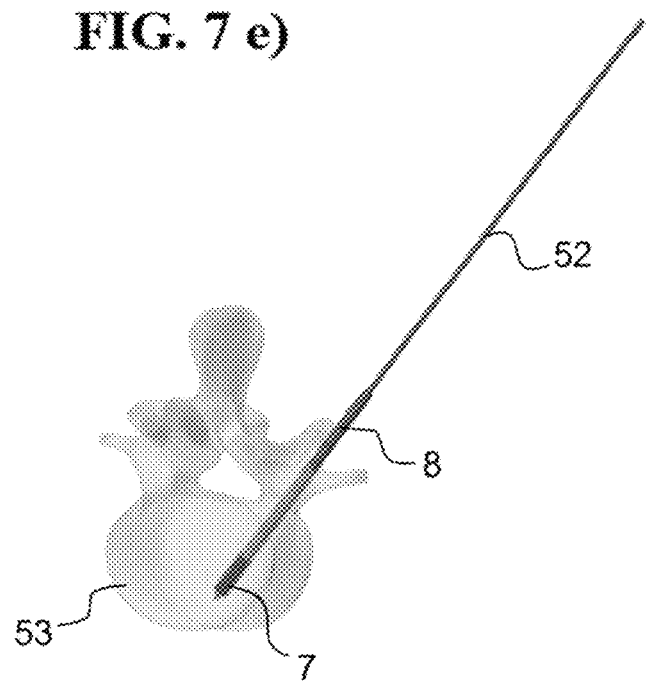
Figure 7:
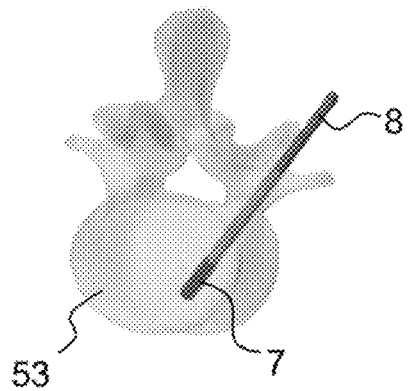
Figure 7:
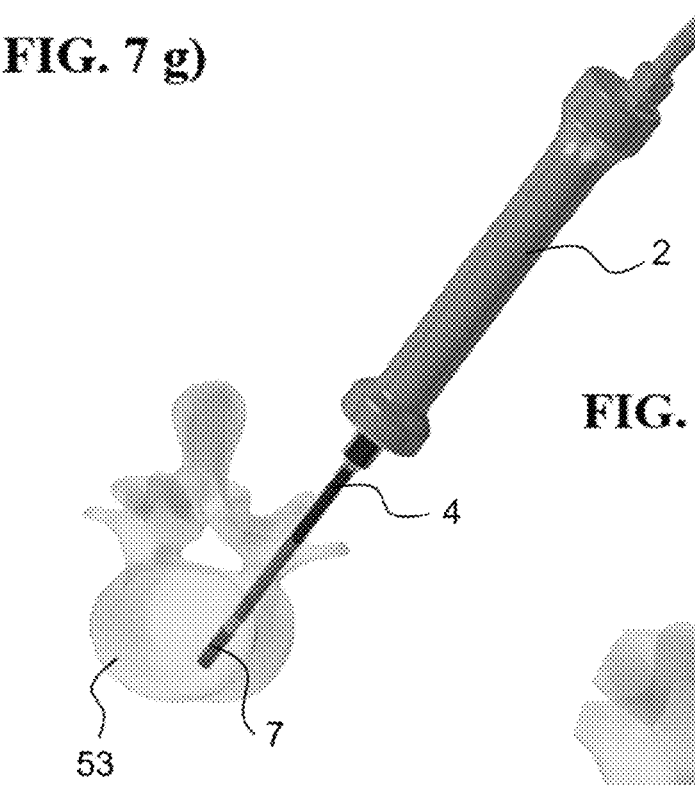
Figure 7:
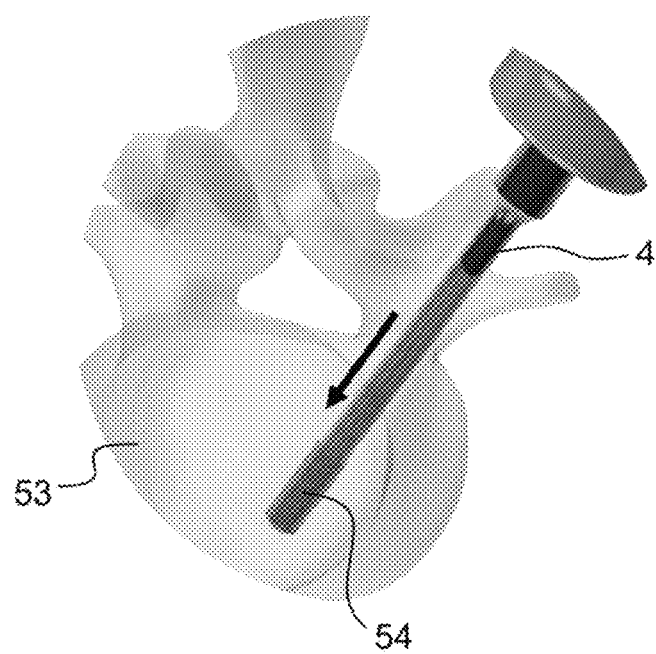
Figure 7:
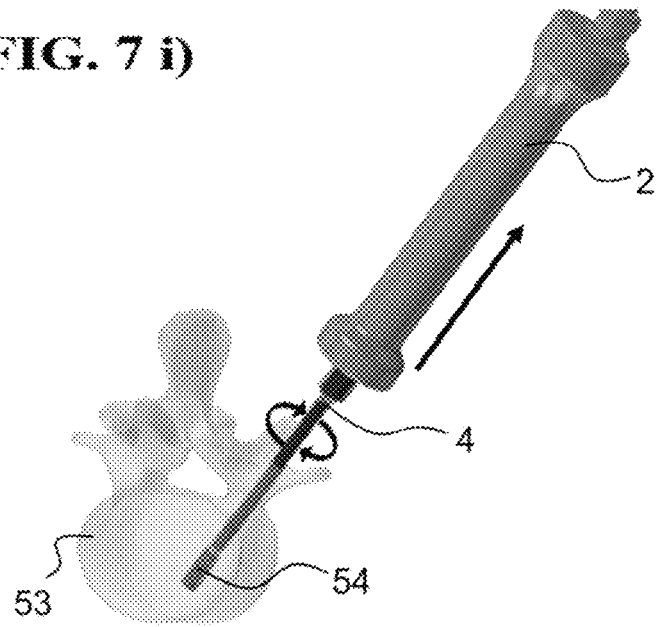
Figure 7:
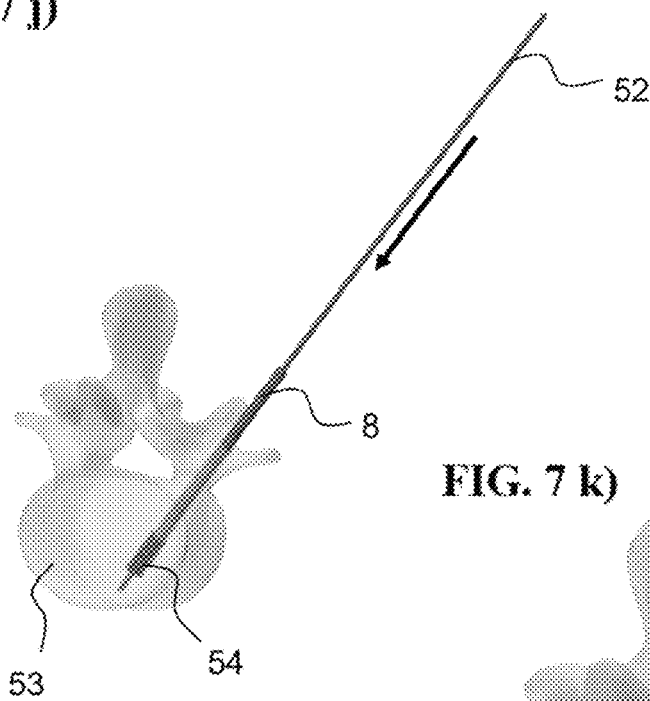
Figure 7:
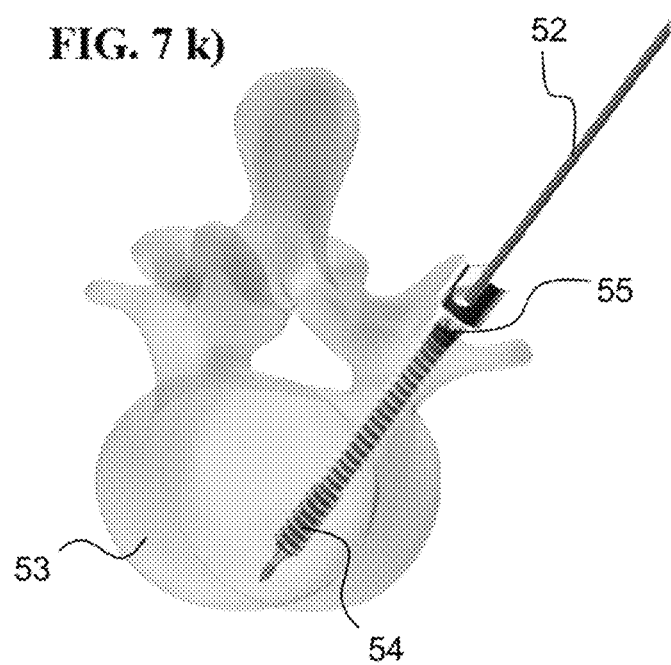
Figure 7:
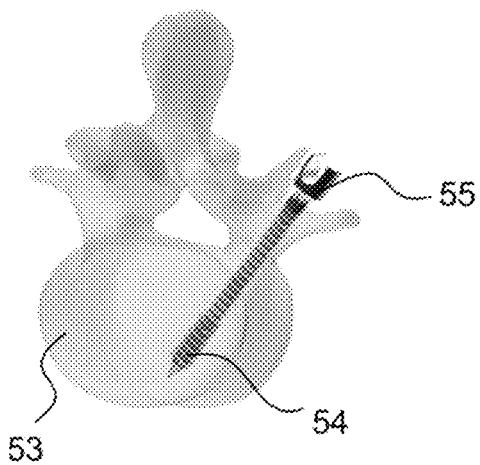

FIG. 1 shows the entire immediate stabilization system with all components required for the immediate stabilization system augmentation process. The ultrasonic (US) generator 1, the handgrip 2 with the covering ring 3, the sonotrode 4 and the ISS sleeve 4 together with the guide pin 8 represent the core-components of the system. The US generator 1 supplies the handgrip 2 (converter) with electrical power, which is converted in the handgrip 2 into a mechanical oscillation. The mechanical oscillation is directed to the Sonotrode 4 that oscillates with a particular amplitude and supplies the polylactide ISS sleeve 7 with the power/energy necessary for melting the material and moulding it into the adjacent trabecular bone structure. Pre-clinical test have shown that this leads to an enhanced mechanical stability of the surrounding bone structure.

Furthermore the system may include an insertion device 5, a reamer 6, the cleaning device 9 and a torque key 10. Furthermore and advantageously the ultrasound generator can be controlled by the operator using a foot pedal 11 (or alternatively a control on the handgrip) controlling the amount of energy generated by the ultrasound generator and transfer to the handgrip 2 and transmitted to the sonotrode 4.

In FIGS. 2a)-2c) a reamer 6 for use in such a system is shown. The reamer comprises handgrip 12 and the actual extension portion 13, which at the tip of it comprises a threaded portion 14. The very tip 15 of the reamer 6 is illustrated in detail in FIG. 2c), the reamer is shown in a side view in FIG. 2a), and in a perspective view in FIG. 2b). Importantly, the reamer 6 comprises a fully penetrating cannulation 17, so this cannulation 17 also penetrates the handgrip 12 and forms the handgrip opening 16 of the cannulation 17. At the tip of the reamer 6 it is forming a tip opening 18 of the cannulation 17. The tip portion has a stepped design in that it comprises a distal front edge 19 adjacent to the tip opening 18, and then a cylindrical transition portion 21 followed by a proximal step portion 20 of the tip. Using this reamer for preparation of the recess 56 leads to a stepped shape at the bottom of the recess simplifying insertion and also improving positioning of the guide pin. FIGS. 3a)-3f) shows the insertion device 5 in various different representations. As one can see the insertion device also comprises handgrip 23 which, by a transition portion 27, is attached to an extension portion 24 which is a cylindrical tubular structure which also has a cannulation. In the extension 24 there is a distal narrow portion of the cannulation 26, and in the handgrip 23 there is a proximal wider portion of the cannulation 25. The cannulation 26 at the tip of the insertion device (see details in FIG. 3d) forms a tip opening 32, and the tip portion of the extension 24 in this region is provided with a front surface and chamfered edges. Importantly, in the tip region there is provided a reduced outer diameter tip portion 29 which is used as a seat for the amelioration sleeve. The outer diameter of this reduced outer diameter tip portion 29 essentially corresponds to the inner diameter of the amelioration sleeve which is used. This portion 29 towards the proximal end of the insertion device ends at the step 30 between the cylindrical outer surface 28 of the extension 24 and the portion 29. This step 30 acts as a stop for an amelioration sleeve shifted onto the tip portion of the insertion device. Preferably the height of the step 30 is somewhat less than the wall thickness of the amelioration sleeve, so that when drawing the insertion device out of the recess after positioning, the amelioration sleeve remains in the recess and is not drawn out together with the insertion device.

FIG. 3f) shows a slightly different particularly advantageous tip design for such an insertion device 5. In this particular case, the tip is represented together with the amelioration sleeve 7 mounted on the reduced outer diameter tip portion 29. This reduced outer diameter tip portion 29 is flattened in region 57/58 on both opposing sides. This flattening extends not only in the reduced outer diameter tip portion 29 but the flattening extends partially into the cylindrical outer surface 28 behind the reduced outer diameter tip portion 29. The advantages of this tip design are as follows: the tip design leads to a better release of the amelioration sleeve 7, because the trabecular bone structure "catches" the sleeve 7 at the surface behind the sleeve 7. As a matter of fact, due to the window 60 formed in the region 58 behind the sleeve 7 the rear edge 59 of the sleeve 7 is exposed and after insertion of the insertion tool with the sleeve into the whole to be ameliorated this edge 59 hooks with the hole to be ameliorated and upon withdrawal of the insertion tool automatically the sleeve 7 remains in the hole in the desired position. Furthermore, by bracing the sleeve 7 in a slightly oval shape, one can increase the manufacturing tolerance of the insertion tool tip and get a higher "clamping" force by means of an increased diameter.

FIG. 4 shows the guide pin for use in such a system. The guide pin 8 is a cylindrical structure of a polymer material that has a central cannulation 35 that is coaxial with the outer surface of the cylinder. Preferably at both ends the guide pin is provided with chamfered portions 38 and 36, the angles of which relative to the main axes may be the same or different. Furthermore the guide pin has a tip opening 37 at 1 and a backside opening 39 at the other end.

FIGS. 5a)-5c) show a sonotrode 4 for use in such a system. The sonotrode comprises a holding portion 41 which preferably as, in diameter, flattened portions 46 and which has a central opening. Furthermore there is an extension portion 40 with and enclosing a cylindrical inner opening 44. In the tip portion this cylindrical opening 44 as a smaller inner diameter than in the proximal portion 45. The tip portion of the sonotrode has a chamfered front edge 43 surrounding the tip opening 47, and the angle between the main axes of the sonotrode for and this chamfered surface is 45°.

FIGS. 6a) and 6b) show an amelioration sleeve 7 for use in such a system. The amelioration sleeve is made of a polylactide material which can be liquefied by ultrasonic energy and which is bio resorbable. It has a cylindrical inner surface 50 the inner diameter of which corresponds to the outer diameter of the guide pin 8. A possible dimensioning of these two devices is that the inner diameter of the amelioration sleeve is $3.65^{-0.05/-0.00}$ mm and the outer diameter of the guiding pin is $3^{-0.02/-0.05}$ mm. So there is a play between the outer diameter of the guiding pin and the inner diameter of the amelioration sleeve. This is desired if only a small amount of material shall be introduced into the porous wall of the hole to be ameliorated. In this case the wall thickness of the amelioration sleeve is 0.3 mm. However if more material is to be used for ameliorating the hole, an amelioration sleeve with the same outer diameter but with an inner diameter of e.g. 3.35 mm can be used amounting to about 50% more material. If even more material shall be available an amelioration sleeve with the same outer diameter and an inner parameter of 3.1 mm can also be used, amounting to almost twice the material of the slim sleeve, and all these amelioration sleeves can be handled with the same sonotrode and guiding pin, which is a huge advantage as it allows for adaptation of the amount of material for amelioration by simply choosing adapted amelioration sleeves without having to change the hardware for inserting the amelioration. The cylindrical outer surface 49 corresponds with its outer diameter typically to the outer diameter of the extension portion 40 of the sonotrode 4 or is somewhat larger and the outer diameter of the extension portion of the sonotrode. The wall portion 51 typically has a thickness of 0.2-0.6, or 0.2-0.4 mm preferably of 0.3 mm.

In the following it shall be illustrated how the proposed method for minimally invasive amelioration can be used in detail in the context of FIGS. 7a)-7l).

As illustrated in FIG. 7a), the method comprises a step of pedicle opening in the vertebra element 53 and channel preparation. Once the access to the pedicle has been exposed, a channel has to be created through the pedicle by means of any standard surgical procedure.

To enable a guided operation procedure, a K-wire (Kirschner Wire) 52 is introduced into the existing channel 56.

The method then comprises a step of implant bed preparation as illustrated in FIG. 7*b*).

The existing pedicle channel is expanded in diameter by means of the ISS reamer 6 for ensuring a precise implant bed. Therefore, the ISS reamer 6 is guided over the previously placed K-wire 52. The reamer 6 is slightly pressed forward, into the pedicle channel, while it is rotated until the final placement depth of the pedicle screw is reached.

The final depth can be recognized by the depth scale which is provided on the shank of the reamer.

The next step as illustrated in FIG. 7 *c*) is the step of ISS sleeve placement. The ISS sleeve 7 is attached to the smaller cylinder at the tip of the ISS insertion device 5.

Then, as illustrated in FIG. 7 *d*), showing the ISS sleeve insertion, the ISS sleeve is placed at the bottom of the implant bed by means of the insertion device 6, guided over the K-wire 52 controlling the insertion depth by the markings on the insertion device 6. Subsequently, the ISS insertion device 6 can be easily removed, leaving the ISS sleeve 7 on its place.

The depth scale indicates at which depth the ISS sleeve should be placed referring to the length of the later implanted pedicle screw and in relation to the prepared implant bed depth (by the reamer).

In the next step, as illustrated in FIG. 7 *e*), showing the insertion of the guiding pin, the ISS guiding pin 8 is inserted into the implant bed and through the ISS sleeve 7 at the end of the pedicle channel. The accurate positioning is ensured by the positioned K-wire 52.

The next step is the step of temporary removal of the K-wire, as illustrated in FIG. 7). In order to perform the ISS melting process, the K-wire needs to be removed temporary.

In the next step as illustrated in FIG. 7 *g*) showing settling the sonotrode oscillation, before starting the US oscillation, the sonotrode 4 is placed slightly over the ISS sleeve 7 inside the implant bed. At the moment of activation, the sonotrode 4 should be free from any fixation or other external forces for ensuring a successful settling of the sonotrode ultrasound oscillation.

In the next step as illustrated in FIG. 7 *h*) of the melting of the ISS sleeve, the ultrasound energy is activated by operating the foot pedal. Simultaneously, the sonotrode 4 needs to be slightly pressed down for melting the ISS sleeve 7 into the surrounding trabecular bone structure. The Ultrasound oscillation will continue as long as the foot pedal is operated but typically not longer than 5 seconds. A depth scale is provided at the lateral surface of the sonotrode 4, indicating the depth which has to be integrated into the bone for ensuring a successful melting of the entire ISS sleeve.

In the next step of removing the sonotrode as illustrated in FIG. 7 *i*) approximately 5 seconds after the ultrasound energy was deactivated again, the molten polymer is re-solidified. By slightly turning the handgrip, the sonotrode 4 will be detached from the molten ISS sleeve and the sonotrode 4 can be easily removed from the implant bed.

The next step is a step of re-insertion of the K-wire as illustrated in FIG. 7 *j*). After the ISS melting process has successfully been completed, the K-wire is re-positioned through the remaining guiding pin 8. Thereafter, the guiding pin 8 is removed from the implant bed via the inserted K-wire 52.

Then follows the step of pedicle screw implantation as shown in FIG. 7 *k*). The pedicle screw 55 implantation can now be done, following the usual standard surgical procedure for the corresponding implant system.

FIG. 7 *l*) shows the finally augmented pedicle screw. After the K-wire has been removed the implantation including the ISS pedicle screw augmentation is completed.

Figure 8:
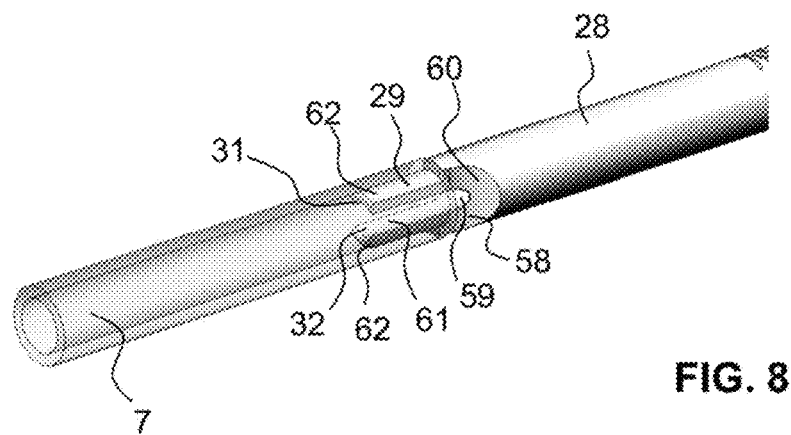
FIG. 8 shows another a modified tip design of the insertion device.

In FIG. 8 another possible design of the tip portion of the insertion device is shown. As in FIG. 30, the tip is represented together with the amelioration sleeve 7 mounted on the reduced outer diameter tip portion 29. This reduced outer diameter tip portion 29 is flattened in region 57/58 on both opposing sides. This flattening extends not only in the reduced outer diameter tip portion 29 but the flattening extends partially into the cylindrical outer surface 28 behind the reduced outer diameter tip portion 29. In this particular case the flattening 57/58 is carried out such that the width of the remaining portion of the tip is smaller than the inner diameter of the cannulation, which means that on both sides slots 61 are formed, and two arms 62 are given.

The advantages of this tip design are as follows: the tip design leads to a better release of the amelioration sleeve 7, because the trabecular bone structure "catches" the sleeve 7 at the surface behind the sleeve 7. Again, due to the window 60 formed in the region 58 behind the sleeve 7 the rear edge 59 of the sleeve 7 is exposed and after insertion of the insertion tool with the sleeve into the whole to be ameliorated this edge 59 hooks with the hole to be ameliorated and upon withdrawal of the insertion tool automatically the sleeve 7 remains in the hole in the desired position. Furthermore, by bracing the sleeve 7 in a slightly oval shape, one can increase the manufacturing tolerance of the insertion tool tip and get a higher "clamping" force by means of an increased diameter. In this embodiment the elasticity of both the amelioration sleeve 7 as well as of the two fingers 62 can be used for holding the amelioration sleeve with just the retaining force as required.

Figure 9:
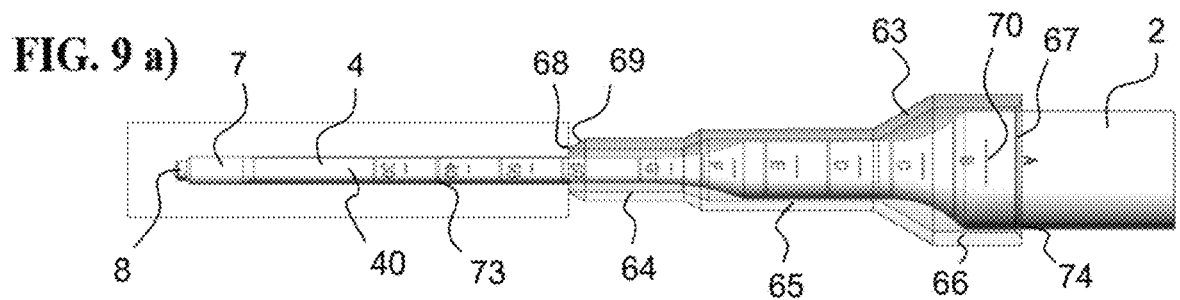
FIGS. 9a)-9c) FIG. 9a show how it is possible to provide markings for the insertion depth of the sonotrode, FIG. 9b) shows how it is possible to provide markings for the insertion depth of the reamer and FIG. 9c) shows how it is possible to provide markings for the insertion depth of the insertion device in conjunction with a protective sleeve.
Figure 9:
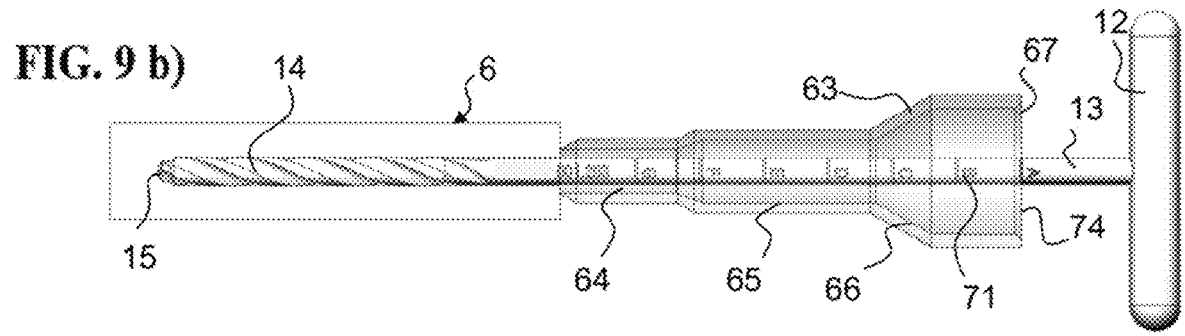
Figure 9:
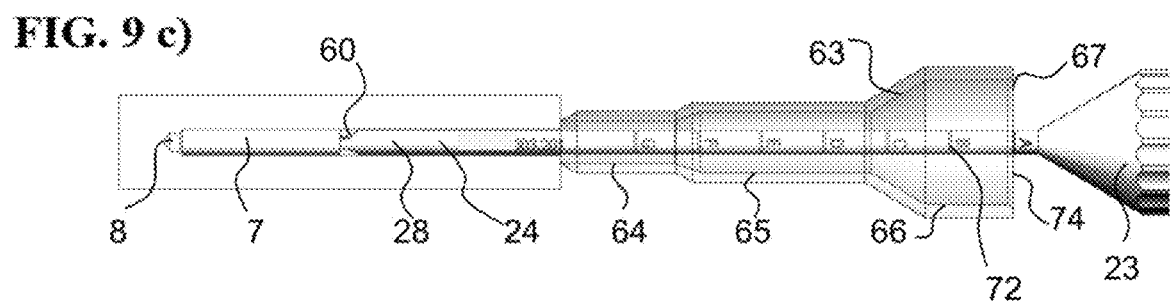

As pointed out above, it can be advantageous to provide for insertion depth markings on the individual tools. In FIGS. 9*a*)-9*c*) this is illustrated for the sonotrode in 9*a*), for the reamer in 9*b*) and for the insertion device in 9*c*). Also illustrated in this representation is a protective sleeve 63 which can be used to protect the surrounding body portions or tissue portions. This protective sleeve 63 comprises three difference portions, a front portion 64, an intermediate portion 65 and a backside portion 66. These portions have an increasing inner and outer diameter and are adapted to the shape in particular of the sonotrode. The front opening 68 has a small diameter and can have a chamfered front edge 69, and the backside opening 67 has a large diameter to take up the handgrip of the sonotrode if fully inserted. Insertion depth markings can either be provided, as illustrated in FIG. 9 *a*), with respect to the actual insertion into the body portion. This is illustrated as marking 73 giving the actual millimeter values of the insertion depth.

Another possibility is to provide insertion depth markings relative to the above mentioned protective sleeve 63 rear side edge 74. For the sonotrode this is illustrated by 70, for the reamer by 71 and for the insertion device by 72.

This simplifies the handling and makes sure that the insertion depth is always measured relative to the same position, since usually the protective sleeve 63 is not removed between the individual steps. For the surgeon it is then easy to use the corresponding appropriate insertion depth by simply choosing one of the insertion depths A-G as given on the corresponding tool.

LIST OF REFERENCE SIGNS 1 ultrasound generator
2 handgrip
3 covering ring
4 sonotrode
5 insertion device
6 reamer
7 amelioration sleeve, stabilization sleeve
8 guiding pin
9 cleaning device
10 torque key
11 foot pedal
12 handgrip of 6
13 extension portion of 6
14 threaded portion of 6
15 tip of 6
16 handgrip opening of cannulation of 6
17 cannulation of 6
18 tip opening of cannulation of 6
19 distal front edge of tip of 6
20 proximal step portion of tip of 6
21 cylindrical transition portion between 19 and 20
22 transition portion between 12 and 13
23 handgrip of 5
24 extension portion of 5
25 proximal wide portion of cannulation
26 distal narrow portion of cannulation
27 transition portion between 23 and 24
28 cylindrical outer surface of 24
29 reduced outer diameter tip portion of 5
30 step between 28 and 29
31 front surface of 5
32 tip opening of cannulation of 5
33 inner surface of 26
34 handgrip opening of cannulation of 5
35 cannulation of 8
36 chamfered tip portion of 8
37 tip opening of 8
38 chamfered backside portion of 8
39 backside opening of 8
40 extension portion of 4
41 holding portion of 4
42 tip portion of 4
43 chamfered front edge of 4
44 cylindrical inner opening in 4 in tip portion
45 cylindrical inner opening in proximal portion
46 flattened portion of 41
47 tip opening of 4
48 cylindrical inner opening in 7
49 cylindrical outer surface of 7
50 cylindrical inner surface of 7
51 wall portion of 7
52 K-wire
53 vertebra element
54 stabilization sleeve penetrated into porosity of surrounding cavity and 53
55 implant, screw
56 recess
57 flattened portion of 29
58 flattened portion of 28
59 free rear edge of 7
60 window
61 slot formed in 58
62 arm of 29
63 protection sleeve
64 narrow front portion of 63
65 intermediate portion of 63
66 while backside portion of 63
67 wide back opening of 63
68 narrow front opening of 63
69 chamfered portion of 64
70 insertion depth markings on sonotrode
71 insertion depth markings on reamer
72 insertion depth markings on insertion device
73 insertion depth marking relative to tissue/bone
74 rear side edge of 63
D outer diameter of 8
d inner diameter of 8

The invention claimed is:

1. A system for the amelioration of a recess, said system comprising:
an element for generating or coupling in mechanical energy,
a guide pin, and
a cylindrical collar with a cylindrical jacket surface having an external diameter and having a central recess for receiving said guide pin,
wherein said guide pin, having an axial central through bore in the form of a cannulation, is provided to be inserted substantially as far as a bottom of the recess under positioning using a wire inserted into said cannulation of the guide pin, before mechanical energy is applied,
wherein said guide pin, in the area of the end thereof directed toward the bottom of the recess, is surrounded by an amelioration sleeve made from a material that can be liquefied by mechanical energy,
wherein the external cylindrical jacket surface of the amelioration sleeve has substantially the same external diameter as the collar,
wherein said guide pin is received movably in the central recess such that, when mechanical energy is applied, the collar can be moved relative to the guide pin in the direction toward the bottom of the recess while liquefying and laterally and/or longitudinally displacing the material of the amelioration sleeve,
wherein said cylindrical collar has a circular cylindrical jacket surface, and the amelioration sleeve has a circular cylindrical jacket surface, and wherein the external diameter of the collar and of the amelioration sleeve are substantially the same as the internal diameter of the recess to be ameliorated,
wherein said cylindrical collar, at its distal end, has a circumferential distal edge tapering toward said distal end,
wherein the amelioration sleeve is a simple hollow cylinder,
wherein said central recess of said cylindrical collar is a circular cylindrical recess which is arranged coaxially with respect to its cylindrical jacket surface,
wherein the amelioration sleeve has a circular cylindrical recess for receiving the guide pin,
wherein the guide pin has a circular cylindrical outer surface, and
wherein the internal diameters of said recesses are substantially the same as the external diameter of the guide pin, or in case of the circular cylindrical recess of the amelioration sleeve, this circular cylindrical recess is larger than the external diameter of the guide pin to adapt for the amount of material to be liquefied.

2. The system according to claim 1, wherein the guide pin, at at least one end thereof has a circumferential edge which is tapering towards the respective end of the guide pin.

3. The system according to claim 1, wherein the guide pin is made of synthetic polymer material.

4. The system according to claim 1,
wherein it further comprises an insertion device for inserting the amelioration sleeve into said recess, and
wherein said insertion device has an axial central through bore in the form of a insertion device cannulation, and is provided to be inserted substantially as far as the bottom of the recess under positioning using a wire inserted into said insertion-device cannulation before said guide pin is to be inserted using the same wire.

5. The system according to claim 1,
wherein it further comprises a reamer for smoothing the inner surface of the recess prior to amelioration thereof, and
wherein said reamer has an axial central through bore in the form of a reamer cannulation, and is provided to be inserted substantially as far as the bottom of the recess under positioning using a wire inserted into said reamer cannulation before an insertion device for the insertion of the amelioration sleeve and/or said guide pin is/are to be inserted using the same wire.

6. The system according to claim 1,
wherein the guide pin can be pushed into the collar at most as far as an abutment position, wherein the guide pin, in this abutment position, ends protruding beyond the collar or at most flush with the distal end of the collar.

7. The system according to claim 1,
wherein the external diameter of the collar is in the range of 1-80 mm,
wherein the external diameter of the guide pin is 0.1-20 mm less, and
wherein the amelioration sleeve has a thickness such that the external diameter thereof is the same as the external diameter of the collar.

8. The system as claimed in claim 1,
wherein the element generates mechanical energy in the form of vibration energy and/or oscillation energy with frequencies in the range of 1 kHz-10 GHz.

9. The system as claimed in claim 1,
wherein the amelioration sleeve is made from a material that can be liquefied by mechanical energy.

10. The system according to claim 1,
wherein it further comprises a handgrip for mounting of a sonotrode or including a sonotrode,
wherein the handgrip is cannulated through its full axial length to allow for the insertion of a wire for accurate positioning in the hole to be ameliorated, and/or
wherein the handgrip has, mounted thereon in an only axially movable manner, attached a tubular protection sleeve, surrounding at least partially the sonotrode and preventing contacting of the sonotrode with surrounding soft tissue located above the bone with the hole to be ameliorated, and/or
wherein the handgrip further comprises means to activate the ultrasonic energy generator for activation of the sonotrode.

11. A guide pin for use in a system according to claim 1, wherein the guide pin, at at least one end thereof, has a circumferential edge which is tapering towards the respective end of the guide pin.

12. A sterile package with a guide pin as claimed in claim 11.

13. A method for operating a system as claimed in claim 1,
wherein a wire is centrally inserted into a recess and pushed into the very bottom thereof,
wherein, if needed the inner surface of the recess is prepared for amelioration by using a reamer with a central cannulation, which cannulation is pushed over said wire for controlled insertion of the reamer into the recess, the reamer being rotated when positioned in the recess until the desired preparation of the recess is terminated, and subsequently the reamer is taken out while keeping the wire in place,
wherein, if needed, an insertion device having an amelioration sleeve mounted at the distal tip portion thereof and having a central cannulation is pushed with said cannulation over said wire for controlled insertion of the insertion device with the amelioration sleeve into the recess and positioning the amelioration sleeve in the bottom region of the recess, and subsequently taking out the insertion device while keeping the amelioration sleeve in the recess and keeping the wire in place,
wherein the guide pin is pushed with its cannulation over said wire for controlled insertion of the guide pin and for insertion of the distal portion thereof into the positioned amelioration sleeve in the recess if an insertion device has been used,
or the guide pin is pushed with its cannulation over said wire for controlled insertion of the guide pin and for insertion of the distal portion thereof into the positioned amelioration sleeve in the recess and subsequently the amelioration sleeve is inserted,
or for inserting the amelioration sleeve together with the guide pin,
wherein the recess has an internal diameter corresponding substantially to the external diameter of collar and amelioration sleeve, until the guide pin abuts against the bottom of the recess and/or engages in a guide taper arranged at the bottom of the recess, and then, with simultaneous liquefying of the amelioration sleeve by applied mechanical energy, if needed using a protection sleeve for protecting surrounding soft tissue, and with pushing of the distal end of the collar into the recess, liquefied material is introduced into cavities, including lateral cavities, adjoining the recess.

14. A method according to claim 13, wherein the method is a non-surgical method.

15. A method according to claim 13, wherein the recess is a recess in an at least partially porous technical material, including wood or wood-like material, or foam material.

16. The system as claimed in claim 1, wherein the recess is a recess in a porous, perforate material having cavities freed by the recess.

17. The system according to claim 1,
wherein the guide pin, at one end thereof, or at both ends, has a circumferential edge which is tapering towards the respective end of the guide pin, and
wherein the inclination angle of the tapering surface with respect to the main axes of the guide pin at the circumferential edge is in the range of 20-60°.

18. The system according to claim 17, wherein the inclination angle is in the range of 30-45°.

19. The system according to claim 1, wherein the guide pin is made of synthetic thermoplastic polymer material, including PTFE and/or PFA.

20. The system according to claim 1, wherein the guide pin has an outer diameter in the range of 1.5-10 mm, and wherein diameter of the cannulation is in the range of 0.5-3 mm.

21. The system according to claim 1, wherein the guide pin has an outer diameter in the range of 2.5-3.5 mm, and wherein diameter of the cannulation is in the range of 1.3-1.75 mm.

22. The system according to claim 1, wherein it further comprises an insertion device for inserting the amelioration sleeve into said recess, wherein said insertion device has an axial central through bore in the form of a insertion device cannulation, and is provided to be inserted substantially as far as the bottom of the recess under positioning using a wire inserted into said insertion device cannulation before said guide pin is to be inserted using the same wire, and wherein the diameter of the cannulation of the guide pin is the same as the diameter of the insertion device cannulation, wherein at its proximal end the insertion device is provided with a handle and/or at its distal end the insertion device, having a cylindrical outer surface at its distal end in as far as inserted into said recess, is provided with a narrowed portion with a reduced outer diameter and a step transition towards the proximal end so as to provide a formfitting structure for temporary holding of the amelioration sleeve for insertion, wherein the cylindrical narrowed portion as well as at least a portion of the cylindrical outer surface of an extension portion of the insertion device adjacent to the narrowed portion is flattened, at opposing sides.

23. The system according to claim 1,
wherein it further comprises a reamer for smoothing the inner surface of the recess prior to amelioration thereof, wherein said reamer has an axial central through bore in the form of a reamer cannulation, and is provided to be inserted substantially as far as the bottom of the recess under positioning using a wire inserted into said reamer cannulation before an insertion device for the insertion of the amelioration sleeve and/or said guide pin is/are to be inserted using the same wire, and
wherein the diameter of the cannulation of the guide pin is the same as the diameter of the reamer cannulation and, in case of using an insertion device the diameter of the insertion device cannulation.

24. The system according to claim 1, wherein the guide pin can be pushed into the collar at most as far as an abutment position, wherein the guide pin, in this abutment position, protrudes beyond this end, wherein the protruding length in the abutment position is 2-3 mm.

25. The system according to claim 1,
wherein the external diameter of the collar is in the range of 2-10 mm, and in that the external diameter of the guide pin is 0.5-1 mm less,
wherein the amelioration sleeve has a thickness such that the external diameter thereof is the same as the external diameter of the collar, and
wherein the amelioration sleeve, at least in some sections, has a wall thickness in the range of 0.2-0.6 mm.

26. The system as claimed in claim 1,
wherein the element generates mechanical energy in the form of ultrasonic oscillations in the frequency range of 30-70 or 50-70 kHz, which are transmitted in the longitudinal, transverse or rotational direction, or in a combination or linear combination of these directions, or substantially exclusively in the longitudinal direction, to the collar and/or guide pin and thus indirectly to the amelioration sleeve, and wherein the collar can be secured on or is part of the sonotrode, and the guide pin can be moved therein, or the guide pin is secured on the sonotrode, and the collar can be moved, or collar and guide pin are secured on a sonotrode or coupled thereto.

27. The system as claimed in claim 1,
wherein the amelioration sleeve is made from a material that can be liquefied by oscillation energy, and that is selected from the following group: thermoplastic biocompatible polymers including polyolefins selected from PP, LDPE, HDPE, UHMWPE, polyoxymethylene, polyaryl ether ketones, including PAEK, PEEK, PEKK, polycarbonates, polyacrylates, including PMMA, polyamides, polyesters, including PET, PBT, polysulfones and polyether sulfones, including PSU, PES and/or biodegradable or resorbable polymers including poly(L-lactide) (PLLA), poly(D,L-lactide) (PDLLA) and/or stereocopolymers thereof with a variable ratio of the L and D,L part, polyglycolides (PGA) and/or copolymers, including polyglycolide-co-trimethyelene carbonate (PGA-co-TMC), poly(D,L-lactide-co-glycolide) (PDLLA-co-PGA) and poly(L-lactide-co-glycolide) (PLLA-co-PGA), poly(e-caprolactone), polydioxanones, trimethylene carbonates (TMC), polyorthoesters (POE) and other polyanhydrides, resorbable polymers which are produced from natural raw materials, including modified polysaccharides (cellulose, chitin, dextran, starch), or a combination or a mixture of these materials,
wherein one or more pharmaceutical active substances can also be provided in this material or this material mixture or applied as a layer on this material, and
wherein these pharmaceutical active substances can be released in a controlled manner.

28. The system according to claim 1,
wherein it further comprises a handgrip for mounting of a sonotrode or including a sonotrode,
wherein the handgrip is cannulated through its full axial length to allow for the insertion of a wire for accurate positioning in the hole to be ameliorated, and/or
wherein the handgrip has, mounted thereon in an only axially movable manner, attached a tubular protection sleeve, made of metal or suitable plastic material, surrounding at least partially the sonotrode and preventing contacting of the sonotrode with surrounding soft tissue located above the bone with the hole to be ameliorated, and/or wherein the handgrip further comprises means to activate the ultrasonic energy generator for activation of the sonotrode, and/or
wherein the system further comprises a wire, in the form of a sterilized stainless steel pin, having a sharpened tip at least at one end, with circular cross-section over its essentially its full-length, and having a diameter in the range of 1.25-1.7 mm.

29. A guide pin for use in a system according to claim 1,
wherein the guide pin, at one end thereof, or at both ends, has a circumferential edge which is tapering towards the respective end of the guide pin,
wherein the inclination angle of the tapering surface with respect to the main axes of the guide pin at the circumferential edge is in the range of 30-45°, and/or
wherein the guide pin is made of synthetic thermoplastic polymer material, including PTFE and/or PFA, and/or
wherein the guide pin has an outer diameter in the range 2.5-3.5 mm, and
wherein the diameter of the cannulation is in the range of 1.3-2.0 mm.

30. The method according to claim 13,
wherein the recess is a recess in an at least partially porous technical material, including wood or wood-like material, or foam material, namely a polymer foam, a composite foam and/or a metal foam, or in an at least partially dead or living porous human or dead or living animal bone section, including in a jaw bone or a spinal column bone, and
wherein the recess is generated at least partially by preliminary drilling.

* * * * *